US006485983B1

(12) United States Patent
Lu et al.

(10) Patent No.: US 6,485,983 B1
(45) Date of Patent: Nov. 26, 2002

(54) SYSTEM FOR ELECTROCHEMICAL QUANTITATIVE ANALYSIS OF ANALYTES WITHIN A SOLID PHASE AND AFFINITY CHROMATOGRAPHIC TEST STRIP

(75) Inventors: Fang Lu, Millbrae, CA (US); Frank N. W. Lu, San Mateo, CA (US); Kai Hua Wang, San Bruno, CA (US)

(73) Assignee: Intec Science, Inc., Brisbane, CA (US)

( * ) Notice: Subject to any disclaimer, the term of this patent is extended or adjusted under 35 U.S.C. 154(b) by 0 days.

(21) Appl. No.: 09/305,771

(22) Filed: May 5, 1999

(51) Int. Cl.[7] ............................................. G01N 33/533
(52) U.S. Cl. ........................ 436/514; 422/56; 422/57; 422/70; 422/82.01; 422/82.03; 422/98; 422/99; 422/110; 427/213.3; 427/213.34; 427/213.35; 436/516; 436/518; 436/530; 436/541; 435/3; 435/7.1; 435/287.7; 435/970; 204/182.7; 204/286; 204/288; 204/290
(58) Field of Search ............................. 422/56, 57, 70, 422/82.01, 82.03, 98, 99, 110; 427/213.3, 213.34, 213.35; 436/516, 514, 518, 530, 541; 435/3, 7.1, 7.93, 287.7, 970; 204/182.7, 286, 288, 290

(56) References Cited

U.S. PATENT DOCUMENTS 4,233,144 A * 11/1980 Pace et al.
5,789,154 A * 8/1998 Durst et al.

* cited by examiner

Primary Examiner—Bao-Thuy L. Nguyen
(74) Attorney, Agent, or Firm—John H. Faro

(57) ABSTRACT

System, method, and test strip for solid phase, electrochemical, quantitative analysis of analytes contained in biological fluid samples. Preliminary to analysis, a test sample solution can be applied to a sample collection pad associated with the solid phase test environment of the test strip. The test sample solution and a test kit reagent are thereby initially contacted, under assay conditions, within this solid phase test environment, and caused to migrate along a fluid pathway therein. Irrespective of the assay format (competitive assay, sandwich assay, etc.), a test kit reagent (e.g. labeled substance) and the analyte of interest (e.g. proteins, hormones or enzymes, small molecules, polysaccharides, antibodies, nucleic acids, drugs, toxins, viruses or virus particles, portions of a cell wall and other compounds which have specific or characteristic markers that permit their identification), either interact with one another to form a complex, or, alternatively, compete with one another for interaction with another test kit reagent, resulting in the concentration of an indicator substance within a delimited area of the solid phase. Thereafter, the delimited area of the test strip is subjected to electrochemical analysis and the results determined by monitoring an electrochemical transition in the form of an indicator, or derivative of the indicator (e.g. indicator species), by potentiostatic or potentiometric quantitative analysis (e.g. anodic stripping voltammetry). This electrochemical transition of the indicator has a characteristic electrical fingerprint that can be measured and which, when compared to a standard, can be correlated with the concentration of the analyte in the sample. This method is suitable for the determination/monitoring of therapeutic range of drugs (anti-convulsants drugs), determination of critical and potentially dangerous levels of endogenous materials which are indicative of disease states (prostate cancer), and numerous other applications presently requiring elaborate and time-consuming clinical laboratory analysis.

12 Claims, 4 Drawing Sheets

SYSTEM FOR ELECTROCHEMICAL QUANTITATIVE ANALYSIS OF ANALYTES WITHIN A SOLID PHASE AND AFFINITY CHROMATOGRAPHIC TEST STRIP

BACKGROUND OF THE INVENTION

1. Field of the Invention

This invention is directed to a system, test method and test strip for electrochemical quantitative analysis of one or more analytes in a test sample. More specifically, this invention is directed to an electrochemical quantitative analysis system for determination of an analyte (e.g. proteins, hormones or enzymes, small molecules, polysaccharides, antibodies, nucleic acids, drugs, toxins, viruses or virus particles, portions of a cell wall and other compounds which have specific or characteristic markers that permit their identification) within a solid phase (e.g. test strip) by measurement of electrochemical changes of label(s) associated with a labeled substance that can be correlated with the concentration of the analyte of interest. The test strip used in this analytical system includes a solid phase affinity chromatographic medium, having an electrochemical detection system associated therewith, within the fluid pathway through said medium. The inventions hereinafter set forth in detail are applicable to quantitative analysis of virtually any analyte, whose concentration can be correlated with an electroactive species of an electroactive substance that is capable of manifesting a change in electrical response within the electrochemical cell-like environment of the test strip of this invention.

2. Description of Prior Art
A. Immunodiagnostics

Immunochemical analysis for an analyte within a solid phase (test strip) generally involves an assay in which an analyte, in a liquid sample, and a labeled substance, interact with each other, or another reaction constituent. Within the context of the prior art, it is understood that a "labeled substance" can, thus, include (a) an analyte mimic that is labeled with an indicator, (b) a labeled ligand that is specific for interaction with the analyte of interest, or (c) a complex that is formed by interaction of (a) or (b) and yet another reaction constituent. The liquid containing the labeled substance and the analyte is then transferred to a porous film or membrane, where it is drawn by diffusion or capillary action along a fluid pathway of the membrane, and encounters one or more companion test kit reagents (at least one of which is immobilized within a definitive area thereof). This labeled substance and/or the analyte is thereafter captured by an immobilized companion test kit reagent at a test site to form a complex. If the complex is present in sufficient concentration, it produces a discernible change at such site. Where the indicator is a pigment, such as a metal (e.g. colloidal gold), or alternatively, a colored latex particle, the discernible change is generally visible to the naked eye.

The following patents are regarded as representative of this type of immunochromatographic assay. These patents are arranged in chronological order and no significance is to be attached to their order of discussion as to the patentability of the invention described and claimed herein.

Campbell et al, U.S. Pat. No. 4,703,017 (assigned to Becton Dickinson) describes a test method for detection of an analyte with a "direct" or "particulate" indicator, specifically an indicator that can be visually detected with the naked eye, thus, making such test method acceptable for home diagnostic use; or, alternatively, in a clinical setting devoid of sophisticated analytical equipment. The direct indicator of choice is a liposome containing a pigment or equivalent colorant. The claimed test method is described as suitable for urine analysis of analytes (e.g. pregnancy test); and, thus, capable of detection of an elevated level of analyte. Accordingly, such assay is regarded as a semi-quantitative determination of the analyte of interest. Because the test involves a single step (e.g. application of the sample to the test strip), the test has become characterized in the art as a "Rapid" test.

Rosenstein, U.S. Pat. No. 5,591,645 (assigned to Becton Dickinson) describes an immunochromatographic test method based upon the principles described in commonly assigned U.S. Pat. No. 4,703,017 (to Campbell et al). The Rosenstein test device incorporates all of the test kit reagent in the "same plane" of the test strip and contemplates applying the sample directly to the test strip to reconstitute the reagents contained therein and, thereby effect the desired analysis. The direct indicator of choice can be selected from a number of equivalent colorants, however, colloidal gold adsorbed to a binding protein (e.g. antibody or antigen) is generally preferred. The claimed test method is described as suitable for urine analysis of analytes (e.g. pregnancy test); and, thus, capable of detection of an elevated level of analyte or a semi-quantitative determination of the analyte of interest. Because the test also involves a single step (e.g. application of the sample to the test strip), the test has become characterized in the art as a "Rapid" test.

Swanson et al, U.S. Pat. No. 5,073,484 (assigned to Abbott laboratories) describes an immunochromatographic test method utilizing multiple test zones, with each zone arranged along a common linear fluid pathway. As the test sample and test kit reagents migrate along this fluid pathway, the analyte of interest (generally associated with a direct indicator) becomes bound to an immobilized companion reagent in each of the test zones. Each of the test zones is precalibrated in reference to a standard, and thus the appearance of color in specific test zone correlated with the concentration level of analyte in the sample. Accordingly, the concentration of the analyte in the sample can be estimated from the level of color development along the fluid pathway of the test device. Because the test also involves a single step (e.g. application of the sample to the test strip), the test has become characterized in the art as a "Rapid" test.

May et al, U.S. Pat. No. 5,602,040 (assigned to Unilever Patent Holdings) describes an immunochromatographic test method analogous to the test methods described in the Campbell et al and Rosenstein patents discussed above. One of principles differences identified and claimed by May et al, is the lyophilization of a sugar, along with the direct indicator, in the sample receiving site. The sugar addition is reportedly required to effect reconstitution of the lyophilized indicator and thus permit its interaction with the analyte in the sample.

With the limited exception of the adaptation of the foregoing Rapid Tests to detection of an elevated level of analyte, these Rapid Tests are generally unsuitable for precise quantitative monitoring an analyte level, or for the quantitative detection and differentiation of more than one analyte within a single test environment.

B. Instrumental Analysis

Analysis of fluid samples has also traditionally involved the use of instrumentation and the measurement of changes in electrical potential and/or current at given site/electrode. Typically, the electrical measurement is referenced to a second electrode, and a number of measurements made over a given interval and/or defined range of conditions.

The following patents are regarded as representative of this type of electrochemical analysis. These patents are arranged in chronological order and no significance is to attach to the order of discussion, or to their relative significance to the patentability of the invention described and claimed herein.

Wang U.S. Pat. No. 5,292,423 (assigned to New Mexico State University Technology Transfer Corp.) describes a method and apparatus for trace metal analysis of fluid samples (e.g. drinking water, blood, urine etc.) by means of initial adsorption of the trace metal from a fluid sample onto a screen printed carbon (working) electrode that had been pre-coated with mercury. The Wang test platform also employs at least one additional (reference) electrode. The electrode having the trace metal was, thereafter, subjected to analysis by either Anodic Stripping Voltammetry (ASV) or Potentiometric Stripping Analysis (PSA). The reported advantages of the Wang method and apparatus include the ability to adapt his invention to on-site field testing of sample fluids for suspected pollutants with a disposable testing device.

Brooks U.S. Pat. No. 5,753,517 (assigned to the University of British Columbia) describes a quantitative immunochromatographic assay utilizing an apparatus for detection of a particulate latex indicator in accordance with the procedures associated with so called RAMP™ technology. According to Brooks et al., the RAMP™ technology utilizes latex particles in a manner similar to enzymes in ELISA assays. In the RAMP™ technology based analysis, a test strip, having two distinct fluorescent labeled indicators, is placed in a cartridge, and a fluid sample applied to the test strip. The analyte of interest interacts with one of the indicators forming a fluorescent complex which is captured in the test zone of the test strip, and while the second indicator remains in tact within the test strip, (so as to provide an internal standard). The RAMP™ technology is, thus, capable of differentiation of the fluorescent complex from the internal standard, and the amount of analyte in the sample determined thereby.

Brooks et al. alternative system for performance of his analysis, contemplate the use of optical detection methods (light scattering) and measurement of changes in electrical conductivity or resistively. In one of the suggested alternatives, Brooks et al. contemplates (U.S. Pat. No. 5,753,517—col. 7, lines 7–19, inclusive) the quantitative measurement of the analyte of interest by the electrochemical detection of a released electroactive agents, such as bismuth, gallium or tellurium ions, from a complex associated with the analyte of interest. According to Brooks et al one of these alternatives involves the use of a chelating agent-protein conjugate as an indicator for the analyte of interest, and detection thereof contemplates the addition of an acidic solution for release the metal label as ions for later quantitation by anodic stripping voltammetry (as described by Hayes et al, Anal. Chem. 66:1860–1865 (1994).

The following published technical literature is regarded as representative of this type of electrochemical analysis. These papers are arranged in chronological order and no significance is to attach to their order of discussion, or to their relative significance to the patentability of the invention described and claimed herein.

Electrochemical techniques have provided challenges associated with affinity-chromatographic reactions, because of their stable and sensitive signal, lower level of detection limit, simple operation and cost-effectiveness. Pioneering studies by Henieman et al.(Hayes, F. H. et al., Anal. Chem., 66, 1860–1865 (1994)) illustrated the use of metal ion labels for heterogeneous immunoassays with Anodic Stripping Voltammetric (ASV) detection. Such immunoassays involved covalently linking chelating agent to a protein to serve as a chelon for the metal label. Following competitive equilibrium between the labeled and unlabeled protein for the antibody (immobilized on the surface of a polyester tube), the metal label was released and transferred to an electrochemical cell for an ASV detection with a hanging mercury drop electrode (HMDE) and a deaerated solution. Similarly, Wang et al. (Wang J., Anal. Chem., 70, 1682–1685 (1998)) employed an antibody-coated, screen-printed sensor, performed the entire assay protocol directly on the surface of the disposable strip, and employed the highly sensitive potentiometric stripping mode for detecting the released metal ion label in microliter solutions. As desired for decentralized sensing applications, such an on-chip protocol offers several advantages compared to conventional ASV-based immunoassays, including simplified operation (e.g., the elimination of the separation and reagent volumes, elimination of toxic mercury drops, and a more sensitive stripping detection mode). The Wang et al. system requires relatively long incubation periods for pre-conditioning the sensor (prior to use) and for interaction with the sample; and, multiple washing steps, both of which make this method impractical and cumbersome.

OBJECTS OF THE INVENTION

It is the object of this invention to remedy the above and related deficiencies in the prior art.

More specifically, it is the principle object of this invention to adapt rapid affinity chromatographic electrochemical analysis to quantitative determination of analytes of interest.

It is another object of this invention to provide a system for electrochemical quantitative analysis of an analyte(s) within a solid phase test format that is comparable in ease of use to rapid immuchromatographic assays.

It is yet another object of this invention to provide a system for electrochemical quantitative analysis of an analyte(s) within a solid phase test format involving a simplified means for detection of labels by potentiostatic or potentiometric measurement of changes within the solid phase that are attributable to the concentration(s) of label(s) within the test site.

It is still yet another object of this invention to provide a system for concurrent electrochemical quantitative analysis of a common test sample for multiple analytes within a solid phase test format involving a simplified means for detection of label(s) by stripping voltammetry

SUMMARY OF THE INVENTION

The above and related objects are achieved with the electrochemical quantitative analysis system, method and test strip of this invention for determination of the concentration of an analyte within a solid phase test environment. Initially, a test sample solution and a labeled substance are initially contacted, under assay conditions, within a solid phase test environment, and caused to migrate along a fluid pathway therein. Irrespective of the assay format (competitive assay, sandwich assay, etc.), the labeled substance is concentrated (bound) within a delimited area of the solid phase. Within the context of the system and analytical method of this invention, a "labeled substance" can include any suitable electroactive material that can be isolated within a delimited area of the solid phase, under assay conditions, or which can release an electroactive component within such delimited area, (also collectively hereinafter referred to as the "electroactive species"); and, such electroactive species thereafter, undergo an electrochemical transition (e.g. redox) incidental to electrochemical quantitative analysis. The observed measurement (transition) of the electroactive species can be directly or inversely related, (e.g. by comparison to a standard curve), to the concentration of the analyte of interest in the test sample.

The two principal types of electroanalytical measurements for determination of the concentration of the analyte of interest are potentiometric and potentiostatic. In each of these analytical protocols, two electrodes are required/involved, and a contacting sample (electrolyte) solution, which together constitute an electrochemical cell-like environment within the test strip. The electrode surface is, thus, the junction between the ionic conductor (e.g. electrolytes from the aqueous fluid sample, test kit reagents, etc.) and an electronic conductor. Within this electrochemical cell-like environment of the test strip, the electrode that responds to the analyte of interest (or an electroactive substance that is indicative of the analyte of interest), is termed the "indicator" or "working" electrode, whereas the electrode that is maintained at a constant potential is termed the "reference" electrode (its response being independent of the sample solution).

In one of the embodiments of this invention, the immobilized labeled substance is contacted with a release reagent to initially cause the release/displacement of the label from the immobilized labeled substance within this delimited area. In the case of a metal label, for example, the released/displaced metal can be further reacted with mercuric ions in the release reagent solution, to form an amalgam on the surface of the working electrode within the delimited area of the solid phase. Thereafter, the delimited area of the affinity chromatographic test strip is subjected to potentiostatic measurement, by anodic stripping voltammetry of the label from the amalgam on the working electrode, which causes the label, to undergo yet a second electrochemical transition, (conversion of the label from the reduced form to the oxidized state). This second electrochemical transition of the label (from the reduced to the oxidized state) has a characteristic fingerprint that can be monitored and which, when compared to a standard curve, can correlate directly with the concentration of the analyte in the sample.

The stripped label from the amalgam and, thus, the analyte of interest, can be quantified by measurement of changes within the delimited area of the test strip by potentiostatic electrochemical techniques. The specifics of this electrochemical quantitative analysis, involve the application of an electrical potential to the delimited area, over a defined range of potentials, and the monitoring the rate of electron transfer (current) at each potential. The variation of electrical potential is analogous to the taking of a series of optical measurement of a colored indicator at varying the wavelengths. The electrical potential applied to the electrode drives (forces) the targeted electroactive species to gain or lose electrons (reduction or oxidation, respectively) at a given rate that is indicative of the concentration of such electroactive chemical species. Accordingly, the resultant current not only reflects the rate at which the electrons move across the electron/solution interface, but also (when compared to a standard), the concentration of the analyte in the test sample. These potentiostatic techniques can, thus, measure any chemical species that is electroactive, (e.g. that can be made to reduce or oxidize within the environment of an electrochemical cell)

One of the preferred designs of the test strip useful in the electrochemical quantitative analysis system of this invention has multiple components and multiple functional areas to (a) control the volume and rate of absorption of sample by the test strip; (b) accommodate the controlled interaction of the sample and a labeled substance with an immobilized binding substance within a delimited area of the test strip; (c) effect the separation of the labeled substance from the endogenous components of the sample; (d), the concentration of the labeled substance within a delimited area of the test strip for electrochemical processing; and, (e) the quantitative determination of the analyte of interest by electrochemical means.

In another of the preferred embodiments of the foregoing test strip design, the sample and the labeled substance can be combined within a bibulous pad (e.g., fiberglass) that is maintained in fluid communication with a solid phase affinity chromatographic test medium. Upon transfer of the sample thereto, the labeled substance is reconstituted, and the resultant labeled substance and/or a complex thereof which is formed with the analyte of interest, drawn into such test medium. As this fluid and its constituents, (e.g. sample, test kit reagent and reaction products thereof), diffuse into and within the affinity chromatographic test medium, the labeled substance becomes bound to a delimited area (also hereinafter "test site") along this fluid pathway. Typically, this delimited area can be defined by means of an immobilized binding substance that is specific for interaction with the analyte, an analyte mimic or a complex of the analyte and/or a labeled ligand (e.g. by binding to an epitope on the analyte). As the analyte, analyte mimic or a complex of the analyte and/or a labeled ligand becomes increasingly concentrated at the test site, it can be measured and the amount thereof correlated with the analyte in the test sample.

The advantages of such controlled potential (potentiostatic) techniques include high sensitivity, selectively toward an electroactive species, a wide linear range, portable & low cost instrumentation and speciation capability.

In order to accommodate multiple functional components within the integral device of the preferred test strip design of this invention, all of the components are preferably arranged/mounted on a common support or backing layer (typically an inert plastic, e.g. Mylar). The substrate of this test device can be pre-printed with a conductive material to afford electrical contact (direct or inductive coupling) between the affinity chromatographic test medium of the test strip and an electrochemical analyzer that is configured to measure subtle electrical changes within the delimited areas in the test strip. As more fully set forth in the description of the Figures, which follows, this support layer is typically imprinted at two or more locations with a conductive material or metal salt, to form what are referred to hereinafter as "electrodes". These electrodes are spatially arranged along the support layer to coincide with delimited areas of the solid phase medium. The electrode coincident with the delimited area of the test site is referred to as the "working electrode". Depending upon the electrochemical method of analysis, the test strip generally requires at least one additional (e.g. "reference" electrode) to form the plates of an electrochemical cell.

Figure 3:
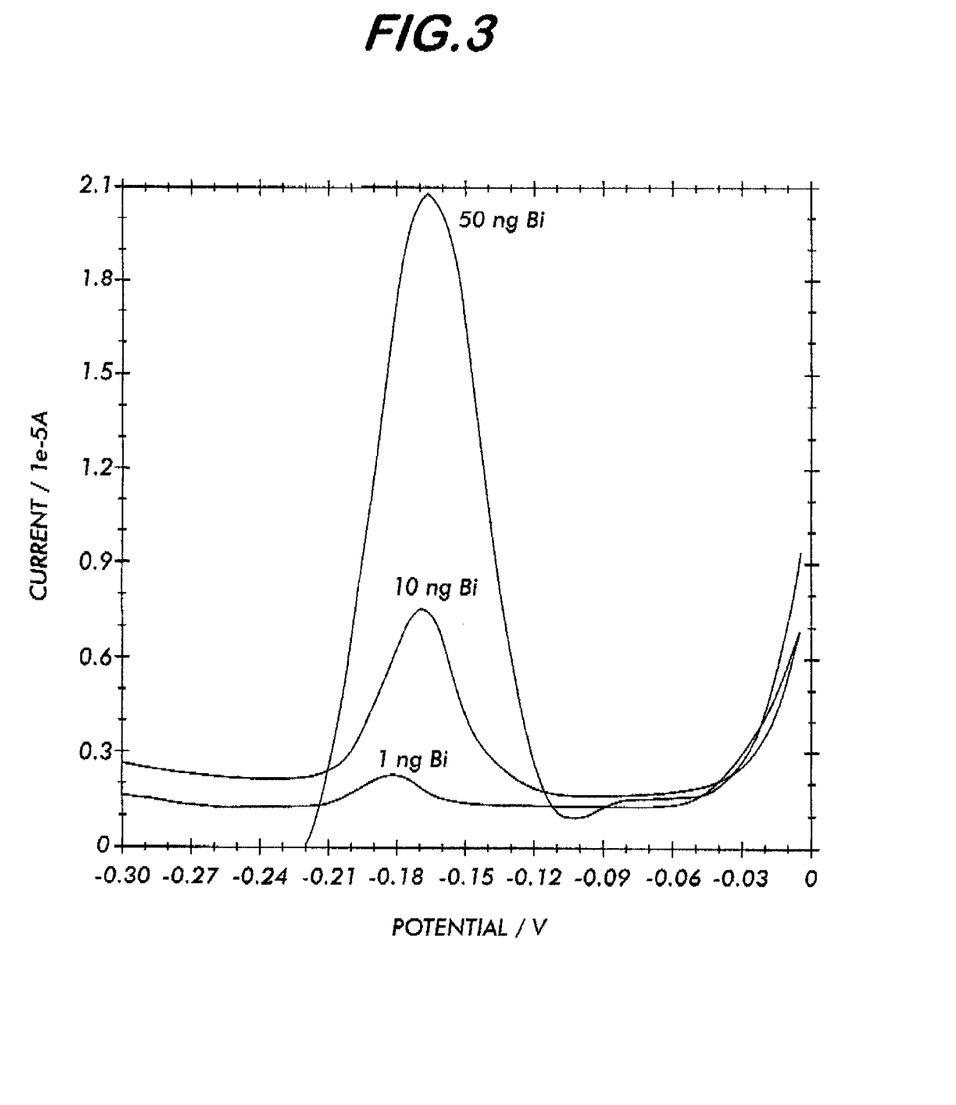
FIG. 3 is a graphical depiction of current signal response of a bismuth/mercury amalgam on a carbon electrode to anodic stripping analysis over a range of concentrations (1 ng/ml to 50 ng/ml of pre-concentrated bismuth metal label).
Figure 4:
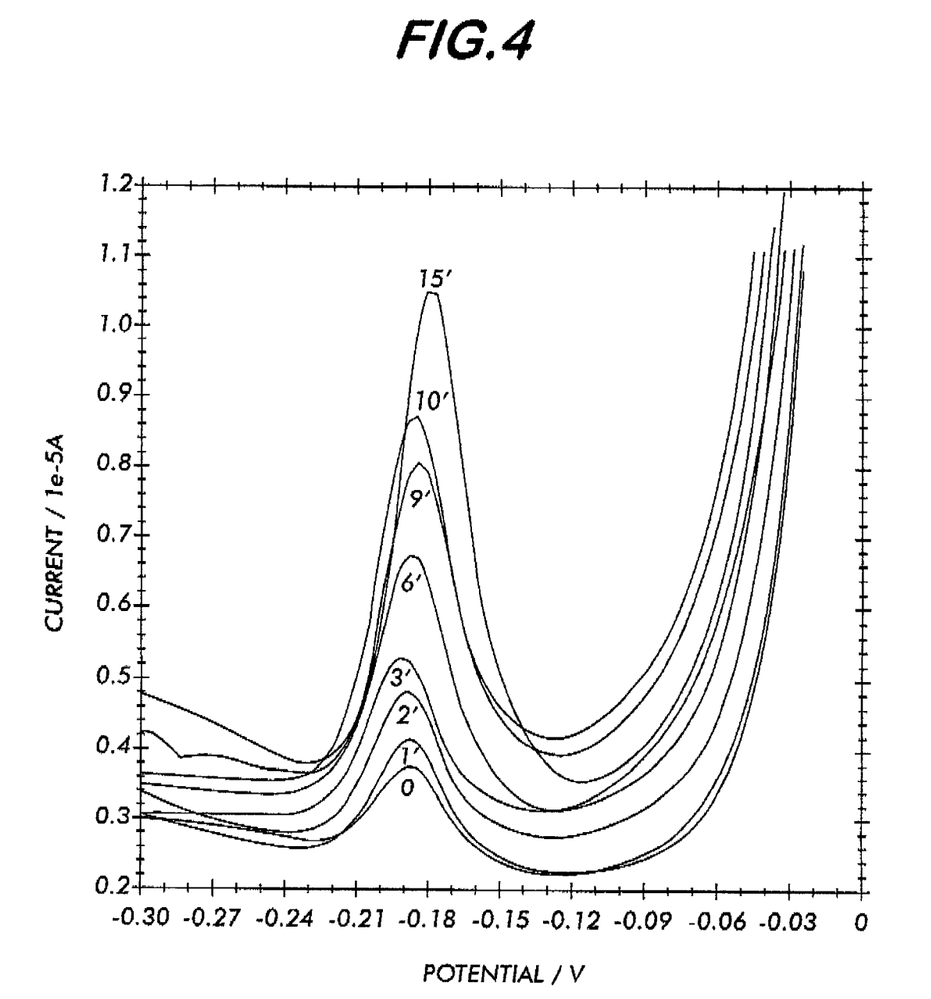
FIG. 4 illustrates the variation in signal (current) intensity, as a function of the duration of "pre-concentration" interval, (prior to electrochemical analysis). In the graphical depiction of this variable shown in FIG. 4, the longer the pre-concentration interval (which varied from 1 to 15 minutes) the greater the current signal intensity.

After having concentrated the labeled substance within the delimited area of the test site, it can be measured by a number of electrochemical techniques. As noted above, it may be desirable, preliminary to performing such measurement, to first isolate the label from the complex by "pre-concentration" thereof on the working electrode. This "pre-concentration" process can involve the release/displacement of the label from the complex and the capture of the label in a reduced form (e.g. amalgam) on the working electrode where it is more electrochemically available or active. Upon completion of this pre-concentration process, the resultant amalgam can be subjected to potentiostatic electrochemical quantitative analysis by anodic stripping voltammetry. In the context of this preferred analytical system (e.g. potentiostatic electrochemical quantitative analysis by anodic stripping voltammetry), the label is reoxidized, under electrochemical quantitative analytical conditions, and this electrochemical transition of the label (from the reduced to the oxidized state) is monitored. The current signal that is generated during this transition (peak and area) is dependent upon a number of system variables, the characteristics of the metal label and the electrode geometry. In each instance, however, these variables can be optimized by empirical adjustment; and, the analysis conditions tailored to correspond to standard curves which are used to correlate electrical signal response to analyte concentration. More specifically, FIG. 3 is a graphical depiction of current signal response of a bismuth/mercury amalgam on a carbon electrode to anodic stripping analysis over a range of concentrations (1 ng/ml to 50 ng/ml of pre-concentrated bismuth metal label). Similarly, FIG. 4 illustrates the variation in signal (current) intensity, as a function of the duration of "pre-concentration" interval, (prior to electrochemical analysis). In the graphical depiction of this variable shown in FIG. 4, the longer the pre-concentration interval (which varied from 1 to 15 minutes) the greater the current signal intensity. Similar correlation/optimization in analytical process conditions is made for each of the labels that are selected and standard curves for each created, as appropriate, to correlate with the dynamic range of conditions likely to be encountered for a given analyte and over a range of concentration.

DETAILED DESCRIPTION OF THE INVENTION INCLUDING PREFERRED EMBODIMENTS

One of the distinct advantages of the system, method and test strip of this invention, is the unique ability to perform concurrent electrochemical quantitative analysis for multiple analytes within a given test sample. Thus, it is possible to perform a drug of abuse panel of assays on a given sample by simply utilizing a different labeled substance for each of the analytes of interest within a given sample. Accordingly, it is understood that the discussion which follows is not intended to either limit the scope or application of the invention to analysis for a single analyte; and, that such description is only limited to analysis to a single analyte for ease of understanding and exemplification.

As noted above in summary fashion, and once again emphasized, the electrochemical, quantitative analysis system of this invention is based upon the initial concentration of a labeled substance within a delimited area of solid phase test environment; and, thereafter, causing an electronic transition in the form of the label, so as to produce a measurable electrical signal within the environment being monitored, which can be correlated with the quantity of the analyte within the test sample.

In certain instances, it may be appropriate (as an intermediate step in the analysis routine) to release/displace the label from the labeled substance, and thereby convert it, or cause it to react with another substance, that permits greater accessibility for electrochemical quantitative analysis. Where for example, the labeled substance is labeled with a metal, (e.g. labeled ligand), the isolation and concentration thereof within the delimited area of the test strip generally requires release and/or displacement thereof from its ligand constituents and the conversion, or reaction thereof, so as to cause/effect its transition to a form (e.g. readily oxidizable or reducible state), which is more readily available for electrochemical state to another. In one of the preferred embodiments of this invention, the labeled ligand is comprised of a functional group that forms a chelate-like coupling to the metal label. This coupling is, however, pH sensitive, and thus, the metal label can be released/displaced from the complex, after concentration within a delimited area of the solid phase, by simply contact thereof with an acidic salt solution.

Alternatively, where the labeled ligand is comprised of an indicator (e.g. metal) encapsulated within a liposome, such as described in Campbell, et al, U.S. Pat. No. 4,703,017 (previously discussed herein), that is in turn conjugated to a ligand, the integrity of liposome capsule can be readily compromised/dissolved with a number of common lipid solvents (e.g. detergents). The metal can, thus, be released from the ligand constituents of the labeled ligand, and made more readily accessible/available for quantitative analysis thereof.

Where the electrochemical quantitative analysis utilizes anodic stripping voltammetry, as the analytical method of choice, the released/displaced metal label can be reacted with mercuric ions within the acidic salt solution to form an amalgam on the working electrode contiguous with the delimited area of the solid phase medium. The electrochemical reduction of the metal label is, thereafter, reversed under subsequent electrochemical quantitative analysis, and the subtle electrical changes monitored during such transition and correlated with the presence and concentration of analyte in the test sample.

Figure 1:
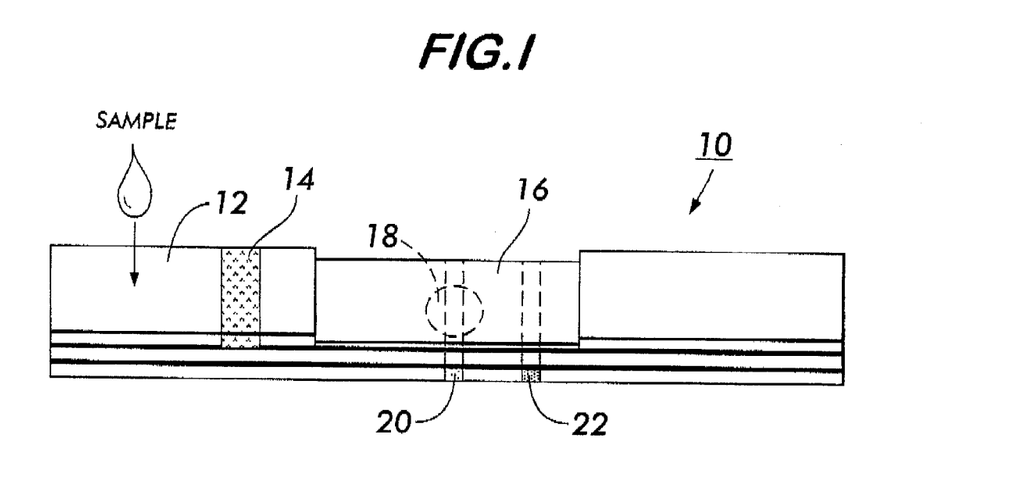
FIG. 1 is an illustration, in perspective, of test strip component of the solid phase, electrochemical, quantitative analysis system of this invention.
Figure 2:
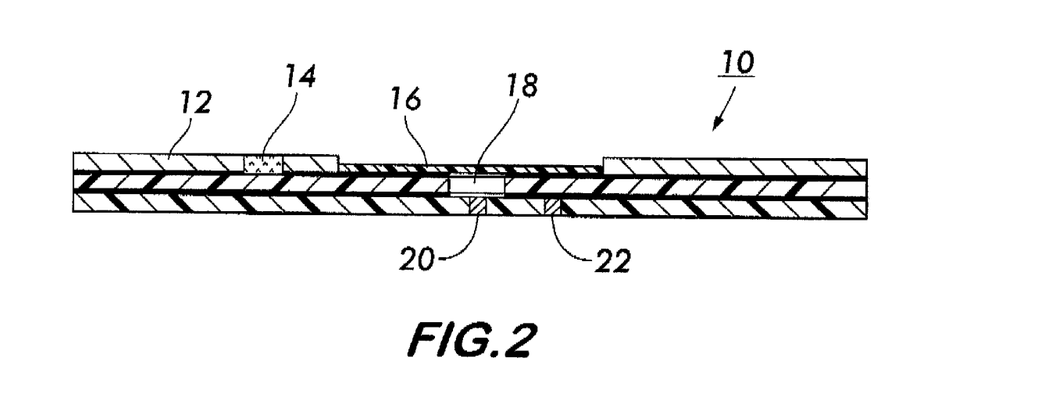
FIG. 2 is a cross-section of the test device of FIG. 1 along plane AA.

In order to provide for ease of use and portability of the system and methods of this invention, the quantitative analysis system of this invention utilizes an affinity chromatographic test strip wherein a delimited area thereof is configured to concentrate the analyte of interest. The test devices illustrated in FIGS. 1 & 2 are representative of a preferred embodiment of this test device.

The test device depicted in these Figures is initially composed of a plurality of discrete areas; and, is preferably, a composite of at least two (2) and more preferably three (3) discrete components, in fluid communication with one another. As shown in FIG. 1, the test device (10) comprises a sample collection pad (12), having labeled substance (14) (e.g. labeled ligand or labeled analyte mimic) pre-disposed within the sample collection pad, either coincident with or contiguous with the sample collection pad (14). In the preferred embodiments of this invention, the labeled substance is lyophilized (to permit stabilization thereof prior to use); and, thereafter reconstituted upon contact with the liquid sample.

Within the context of the system and analytical method of this invention, a "labeled substance" can include any suitable electroactive material that can be isolated within a delimited area of the solid phase, under assay conditions, or which can release an electroactive component within such delimited area, (also collectively hereinafter referred to as the "electroactive species") and, thereafter, undergo an electrochemical transition (e.g. redox) incidental to electrochemical quantitative analysis. The observed measurement (transition) of the electroactive species can be directly or inversely related, (e.g. by comparison to a standard curve), to the concentration of the analyte of interest in the test sample.

In the preferred embodiments of this invention, the labeled test kit reagent is typically comprised of a protein or ligand associated with a metal label. Upon contact thereof with the sample, this metal labeled reagent interacts with the analyte of interest in the sample to form a complex. A labeled substance, which can be utilized in the affinity chromatographic isolation/concentration of the analyte of interest, comprises and a protein/ligand and a metal label that is preferable prepared in accordance with the procedures described in U.S. Pat. No. 4,732,974 (which is herein incorporated by reference in its entirety). In brief, a metal label can be conjugated to the protein/ligand specific for the analyte, by initial modification of the protein/ligand by covalently binding thereto of an "exogenous chelating group" having an affinity for the metal label. The chelating groups specific for the metal indicator of interest, can be covalently coupled directly to the binding protein/ligand or indirectly coupled through an intermediate or linking group. The coupling site must of course be remote from the immuochemically active site that is specific for the analyte of interest. Metal labels that are particularly suitable for use in the synthesis of the labeled substances, that can be used as the test kit reagents in the systems and methods of this invention, include Mg, Al, Ca, Sc, Ti, V, Cr, Mn, Fe, Co, Ni, Cu, Zn, Ga, Sr, Y, Zr, Mo, Tc, Pd, Cd, In, Sn, Sb, Ba, Hf, W, Re, Hg, Tl, Pb, La, Ce, Rh, Pr, Nd, Sm, Eu, Gd, Tb, Dy, Ho, Er, Yd, Th, U, Pu and the isotopes thereof.

Another of the labeled substances that can be utilized in the affinity chromatographic isolation/concentration of the analyte of interest comprises an analyte mimic coupled to a liposome. The preparation of liposome labeled inmunoreagents, and their use in affinity chromatographic assays, is well-known and documented in the technical literature, Roberts, et al, Investigation of Liposome-Based Immunomigration Sensors for the Detection of Polychlorinated Biphenyl, *Anal. Chem*, Vol. 57, No 5 (Feb. 1, 1995) pp. 482–491.

The labeled substance and/or complex of the labeled substance and the analyte, is carried by diffusion/capillary action from the sample application pad along the fluid pathway of the solid phase affinity chromatographic medium (16) to a downstream test site (18) where it is concentrated and immobilized. This can be accomplished in the traditional manner, by the use, for example, of a companion test kit reagent in the form of an immobilized binding protein or other expedient, that is specific for interaction with the analyte/metal complex. Thus, as the labeled substance and/or complex migrates/diffuses along the fluid pathway of the test device, it encounters the immobilized binding substance, and is thereupon captured so as to accumulate at the test site. After a suitable reaction period, sufficient analyte/labeled substance has accumulated in the delimited area of the test strip to provide the requisite amount to be detected and quantified by electrochemical analysis.

The detection and measurement of the quantity of the analyte in the sample is accomplished by means of equipment that can measure subtle electrochemical changes assosicated with an electroactive species, as for example, changes in current or voltage caused by the transition of such species form the reduced to an oxidized form. In practice, this can be accomplish by insertion of the affinity chromatographic test strip of this invention into a suitable measuring device and thereby electrically coupling the device, to electrodes (20) at the test site (18). The electrical coupling of the monitoring instrument to the affinity chromatographic test strip can be by direct (physical contact) or indirect (inductive) coupling of the instrument to the electrodes associated with the delimited area/test site of the test device. The test device is also electrically concurrently coupled to the test strip at another location (22), to provide a point of reference or internal standard for comparison of readings at the test site. Thereafter, an electrical potential is applied to the test site to excite/convert the label from one form/state to another, and such transition monitored. This transition is manifest in a number of ways, depending upon the nature and/or magnitude of the electrical force applied to the test site, and other system variable relating to pre-concentration and the inherent characteristics of the label.

EXAMPLES

The Examples that follow further define, describe and illustrate a number of the preferred embodiments of the test kit reagents and electrochemical methods of analysis of this invention. Apparatus and techniques used in the synthesis of the materials described/used in these Examples are standard, unless otherwise indicated. Parts and percentages appearing in such Examples are by weight, unless otherwise indicated.

Example 1

A. Preparation of Materials

1. Preparation of $Bi^{3+}$ Labeled Ligand 0.1 g DTPA and 0.174 ml Triethylamine were dissolved in 2 ml water with gentle heating. The resulting solution was lyophilized to yield a glassy residue and then such residue was dissolved in 2 ml acetonitrile with gentle heating. This solution was added to 0.034 ml isobutychloroformate in an ice bath during stirring for half hour. The resulting anhydrided, DTPA (127 mM), was then reacted with anti-HCG, anti-HBsAg or anti-Myoglobin MAB antibody in 10 mM PBS, pH7.2 at a molar ratio of 100:1 at room temperature for one hour. The reaction mixture was then dialyzed against 0.5L of citrate buffer (0.25M, pH5.5) at 4° C., changing the buffer solution three times for every one hour and the fourth time, for overnight (Note: remove away the free anhydrided DTPA). 0.5 ml, 100 mM excess of $Bi^{3+}$ was added to 1 ml dialyzed solution and incubated for one hour at room temperature. The $Bi^{3+}$ labeled protein was dialyzed against 0.5 L of phosphate buffer solution (10 mm, pH7.2) at 4° C., changing the buffer solution three times for every one hour and the fourth time, for overnight (Note: remove away the free metal ions).

B. Preparation of Affinity Chromatography Solid Phase Test Device

Two conductive deposits or areas, corresponding to the test site (carbon ink electrode), and the reference site (Ag/AgCl ink electrode) are ink jet printed on a polyester lamina. The size of each printed area is ~5×5 mm and approximately 5/1000 inch thick. After printing, the lamina was dried at 85° C. for one hour.

A nitrocellulose membrane, having an immobilized ligand predisposed at the test site (detection zone), was laminated to the backing layer so as to align the test site with the carbon ink electrode system. A fiberglass pad (containing the metal/ligand conjugate) and excess fluid absorbent medium are each position relative to each end of the laminate to form the assembled test device. The test device fabricated in accordance with this Example is depicted in FIGS. 1 & 2.

C. Measurement of the Analyte

In the course of performance of an assay for HCG, HBsAg or Myoglobin utilizing the foregoing $Bi^{3+}$ labeled ligand and affinity chromatographic solid phase test device, a liquid sample is first applied to the sample application region followed by the migration of the liquid sample by capillary action along the affinity chromatographic strip towards the other end of the affinity chromatographic strip. As the liquid migrates within the sample application pad, and reconstitutes the labeled ligand contained therein, analyte(s) in the sample react with the labeled ligand forming a complex which is transferred to and drawn into the affinity chromatographic test medium. When the complex reaches the detection region (test site), the analytes in the complex react with the immobilized ligand in the detection region forming a labeled ligand-analyte-ligand complex, while the unbound constituents and fluid fraction continue to be drawn and flow into the absorbent medium at the opposite end of the device. The formation of the complex in the detection region is then registered and the labeler $Bi^{3+}$ quantified by the Square Wave Stripping Voltammetry (SWSV). As described above, this stripping procedures involves preconcentration (or formation adsorptive accumulation of a surface-active complex) and determination of the $Bi^{3+}$.

Figure 5:
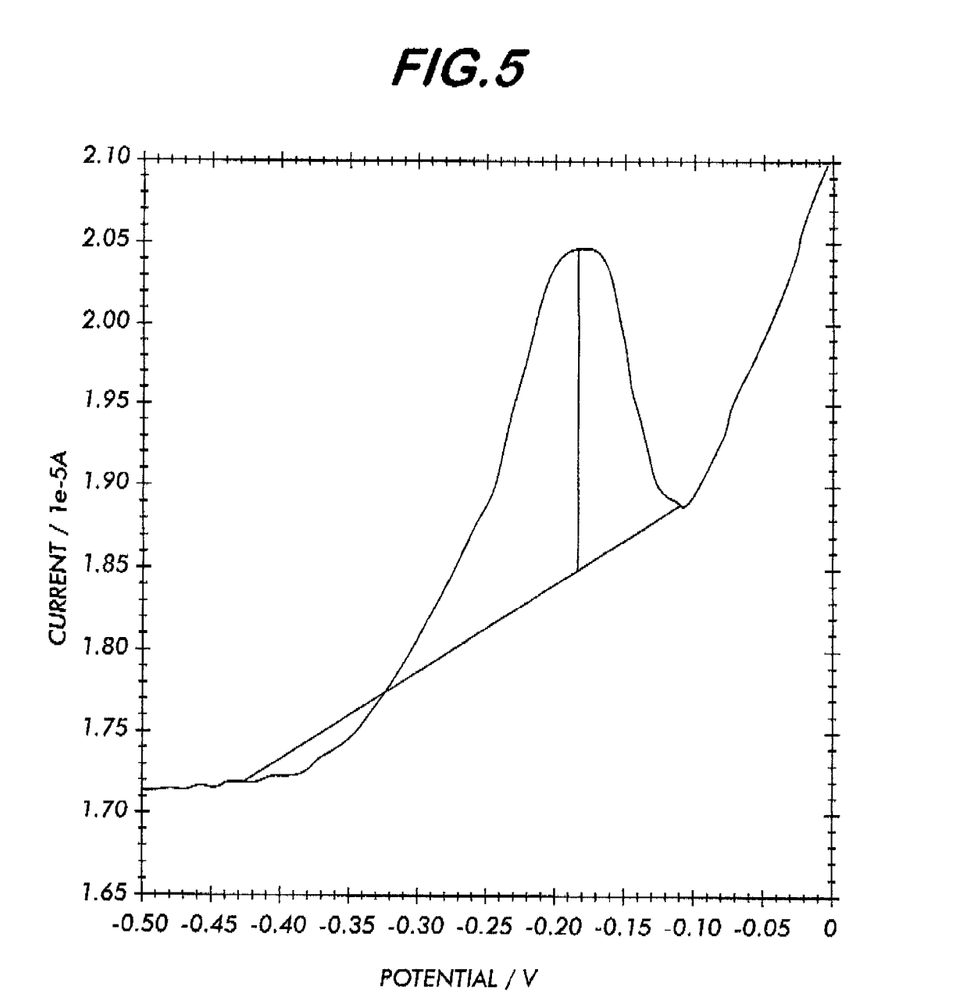
FIG. 5 is a graphical illustration of the electrochemical analysis of a standard solution Myoglobin antibody in accordance with the system, method and test strip (FIGS. 1 & 2) of this invention.

The foregoing analysis is particularly advantageous where the test sample contains endogenous materials that can interfere with more traditional optical measurement techniques, such as is the case of a Myoglobin assay. FIG. 5 graphically illustrates an electrochemical analysis of a standard solution (containing 420 ng/ml of Myoglobin antibody), conducted in accordance with the foregoing system and test method. The low detection limits and sensitivity of this assay due, in part, to the high molar labeling ratio of bismuth ions relative to the anti-Myoblobin antibody, and the duration of the interval of pre-concentration of the bismuth on working electrode.

What is claimed is:

1. A system suitable for concurrent electrochemical, quantitative determination of multiple analytes, in a common test fluid sample, utilizing stripping voltammetry, said system consisting essentially of:
   A. at least one test kit reagent comprising an electrochemically active labeled substance that is specific for binding interaction with an analyte of interest or mimicking of an analyte of interest within said analyte determination system;
   B. a solid phase, porous, electrochromatographic medium having a common, linear fluid pathway defined therein, said linear pathway having a delimited area containing at least one immobilized binding material specific for binding to at least one labeled substance or to a complex of a labeled substance and an analyte suspected of being present in said common fluid test sample;
   C. a sample absorbing means, in fluid communication with said electrochromatographic medium, for combining said test kit reagent(s) and a fluid test sample suspected of containing one or more analytes of interest;
   D. electrode means coincident with and in spaced-apart relationship with said delimited area of said medium, said electrode means comprising an electrochemical cell including at least one working electrode and second electrode selected from the group consisting of a reference electrode and a counter electrode;
   E. means for pre-concentration of an electrochemically active label from said electrochemically active labeled substance by electrolytic displacement of said electrochemically active label from said labeled substance(s), and/or from said complex(es) of a labeled substance and analyte(s), within said delimited area of said medium, so as to cause said electrochemically active label to form a deposit upon said working electrode of said electrochemical cell;
   F. means for activation of said electrochemical cell so as to strip said label from said working electrode by stripping voltammetry and thereby produce a current signal response indicative of the concentration of said analyte(s) of said common test fluid; and
   G. means for monitoring of said electrochemical cell for a current signal resulting from said stripping voltammetry, and thereby correlating said current signal with the presence of said analyte(s) of interest.

2. The system of claim 1, wherein the solid phase, porous electrochromatographic medium includes a second delimited area and a second means for establishing electrical contact therewith under assay conditions, and means for comparison or reference thereof to said electrochemical changes, characteristic of said label(s).

3. The system of claim 1, wherein the label is a metal selected from the group consisting of Mg, Al, Ca, Sc, Ti, V, Cr, Mn, Fe, Co, Ni, Cu, Zn, Ga, Sr, Y, Zr, Mo, Tc, Pd, Cd, In, Sn, Sb, Ba, Hf, W, Re, Hg, Tl, Pb, La, Ce, Rh, Pr, Nd, Sm, Eu, Gd, Tb, Dy, Ho, Er, Yd, Th, U, Pu and the isotopes thereof.

4. The system of claim 1, wherein the labeled substance comprises an analyte mimic, a complex of an analyte mimic a labeled ligand or a liposome containing a label.

5. The system of claim 1, wherein said concentration of said label is determined by potentiostatic measurement of said signal.

6. The system of claim 1, wherein said concentration of said label is determined by potentiometric measurement of said signal.

7. The system of claim 1, wherein the solid phase, porous electrochromatographic medium is further characterized as having a second delimited area and a second means for establishing electrical contact therewith, and means for comparison or reference thereof to said electrochemical changes, characteristic of said label(s).

8. The system of claim 1, wherein the label is a metal selected from the group consisting of Mg, Al, Ca, Sc, Ti, V, Cr, Mn, Fe, Co, Ni, Cu, Zn, Ga, Sr, Y, Zr, Mo, Tc, Pd, Cd, In, Sn, Sb, Ba, Hf, W, Re, Hg, Tl, Pb, La, Ce, Rh, Pr, Nd, Sm, Eu, Gd, Tb, Dy, Ho, Er, Yd, Th, U, Pu and the isotopes thereof.

9. The system of claim 1, wherein the label comprises a liposome containing a substance that is electroactive.

10. The system of claim 1, wherein said concentration of said label is determined by potentiostatic measurement of said signal.

11. The system of claim 1, wherein said concentration of said label is determined by potentiometric measurement of said signal.

12. A method for the concurrent electrochemical, quantitative determination of multiple analytes of a common fluid sample, in a solid phase, comprising:

A. Providing at least one test kit reagent comprising an electrochemically active labeled substance that is specific for binding interaction with an analyte of interest or mimicking of an analyte of interest within said analyte determination system;

B. Providing a test device which includes
  (1) a solid phase, porous, electrochromatographic medium having a common, linear fluid pathway defined therein, said linear pathway having a delimited area containing at least one immobilized binding material specific for binding to at least one labeled substance or to a complex of a labeled substance and an analyte suspected of being present in said common fluid test sample;
  (2) a sample absorbing means, in fluid communication with said electrochromatographic medium, for combining said test kit reagent(s) and a fluid test sample suspected of containing one or more analytes of interest;
  (3) electrode means coincident with and in spaced-apart relationship with said delimited area of said medium, said electrode means comprising an electrochemical cell including at least one working electrode and second electrode selected from the group consisting of a reference electrode and a counter electrode;

C. Applying a fluid sample suspected of containing analytes of interest to said sample absorbent means, so as to combine said sample with and said labeled reagent (s),
  whereby said fluid sample and said labeled reagent(s) are thereby combined and transferred to said solid phase, porous electrochromatographic medium, and thereupon flow along said medium, to said delimited area thereof and become bound within said delimited area; and D. Pre-concentrating said labeled substance on a working electrode of said electrode means, by initially displacing said labeled substance(s) from said delimited area of said solid phase, porous electrochromatographic medium so as to cause said labeled substances to form a deposit upon said working electrode of said electrochemical cell;

E. Stripping said deposit from said working electrode by means of stripping voltammetry; and F. Monitoring said test device for a current signal resulting from said stripping voltammetry, and thereby correlating said current signal with the presence of said analyte(s) in said common test fluid.

* * * * *